(12) United States Patent
Lallier et al.

(10) Patent No.: US 7,959,767 B2
(45) Date of Patent: Jun. 14, 2011

(54) DIMETHYL SULFOXIDE FORMULATION IN MIXTURE WITH ADDITIVE FOR LOWERING THE CRYSTALLIZATION POINT OF SAME, AND APPLICATIONS OF SAID MIXTURE

(75) Inventors: Jean-Pierre Lallier, Saint Bonnet de Mure (FR); Fabienne LeVilain, Sainte-Foy-les-Lyon (FR)

(73) Assignee: Arkema France, Colombes (FR)

( * ) Notice: Subject to any disclaimer, the term of this patent is extended or adjusted under 35 U.S.C. 154(b) by 77 days.

(21) Appl. No.: 12/525,602

(22) PCT Filed: Jan. 28, 2008

(86) PCT No.: PCT/FR2008/050127
§ 371 (c)(1),
(2), (4) Date: Oct. 13, 2009

(87) PCT Pub. No.: WO2008/107611
PCT Pub. Date: Sep. 12, 2008

(65) Prior Publication Data
US 2010/0035784 A1      Feb. 11, 2010

(30) Foreign Application Priority Data
Feb. 5, 2007   (FR) ..................................... 07.53055

(51) Int. Cl.
*C11D 7/50*      (2006.01)
(52) U.S. Cl. .......... 203/64; 510/201; 510/212; 510/407; 134/38
(58) Field of Classification Search ............ 203/64; 510/201, 212, 407; 134/38
See application file for complete search history.

(56) References Cited

U.S. PATENT DOCUMENTS

| | | | |
|---|---|---|---|
| 4,395,479 A | 7/1983 | Ward et al. | |
| 4,401,747 A | 8/1983 | Ward et al. | |
| 4,401,748 A | 8/1983 | Ward et al. | |
| 5,798,323 A | 8/1998 | Honda et al. | |
| 6,103,682 A * | 8/2000 | Lallier | 510/212 |
| 6,414,194 B1 * | 7/2002 | Bloom et al. | 568/27 |
| 6,635,604 B1 * | 10/2003 | Halliday et al. | 507/136 |
| 2001/0034313 A1 | 10/2001 | Honda et al. | |
| 2008/0200383 A1 | 8/2008 | Jennings et al. | |
| 2010/0035784 A1 * | 2/2010 | Lallier et al. | 510/174 |

FOREIGN PATENT DOCUMENTS

| | | |
|---|---|---|
| GB | 2299812 | 10/1996 |
| JP | 1986308848 | 7/1988 |
| JP | 64-42653 | 2/1989 |
| WO | WO 03/048393 | 6/2003 |

OTHER PUBLICATIONS

"Nouveaux decapants peintures a base de DMSO", Lallier, J-P., Double Liaison-Physique et Chimie des Peintures et Adhesifs. No. 467-468, 1995.
"Stability of the Amorphus State in the System Water-Glycerol-Dimethylsulfoxide", Boutron, P. et al., Cryobiology 15(1), 93-108 (1978).

* cited by examiner

*Primary Examiner* — Gregory E Webb
(74) *Attorney, Agent, or Firm* — Steven D. Boyd

(57) ABSTRACT

The invention concerns the use of at least one diol and/or of at least one trial as a an additive to dimethylsulfoxide (DMSO®) in order to lower the crystallization point of same. The DMSO formulation is used in combination with the aforementioned additive as a paint-stripping composition, a surface-cleaning composition, a graffiti-cleaning composition, a surface-cleaning composition in the microelectronics field as a photoresist stripping agent, a DMSO-based agrochemical composition or as a constituent of an aforementioned composition, as a solvent for dissolving polymers, or as a constituent of a composition that is usable in the field of cosmetology or pharmacy.

9 Claims, 1 Drawing Sheet

DMSO PUR

Figure 1:
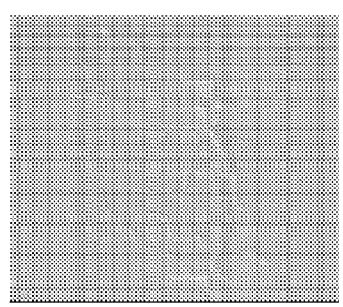

DMSO / GLYCEROL
(90 / 10)

DMSO / eau
(90 / 10)

DMSO / MEK
(30 / 70)

DMSO / GLYCEROL / MEK
(27 / 3 / 70)

DIMETHYL SULFOXIDE FORMULATION IN MIXTURE WITH ADDITIVE FOR LOWERING THE CRYSTALLIZATION POINT OF SAME, AND APPLICATIONS OF SAID MIXTURE

FIELD OF THE INVENTION

The present invention relates to dimethyl sulfoxide and to its various uses. The invention relates to the use of a mixture of dimethyl sulfoxide (DMSO) with an additive for lowering the crystallization point thereof without impairing its efficacy for the usual uses thereof, such as, but without being limited to, paint stripping and the cleaning of surfaces and graffiti. The invention also relates to stripping and cleaning compositions comprising such a mixture.

BACKGROUND OF THE INVENTION

DMSO, a very polar solvent, is particularly suitable for formulating paint strippers generally in combination with a moderately polar cosolvent, such as an ether, a ketone, an ester, etc., which makes it possible to maintain the efficacy of DMSO while reducing the cost of the mixture. Certain combinations lead to true synergistic results, which, depending on the type of paint and on its degree of ageing, are equivalent or similar to the efficacy of the standard combination: methylene chloride+methanol (Double Liaison, Physique et Chimie des Peintures et Adhésifs—No. 467-468-1995 <<Nouveaux décapants à base de DMSO®>>[Double Bond, Physics and Chemistry of Paints and Adhesives—No. 467-468, 1995: "Novel DMSO-based strippers"], J. P. Lallier. It may be noted that protic solvents, i.e. solvents comprising an X—H organic function, X possibly being O, N or S, such as water and alcohols, are not indicated as cosolvents.

However, one drawback of DMSO is its excessively high crystallization point, equal to 18° C., which leads to storage problems, especially when outdoors in winter, and to handling problems at low temperature.

It is known that water can lower the crystallization point of DMSO: a 92.5/7.5 (w/w) DMSO/water mixture has a crystallization point of 0° C. However, the addition of water to a DMSO-based formulation entails a certain number of problems relating to the formulation and to the application:
- during formulation, the water associates very strongly with the DMSO, giving rise to a highly hydrophilic and polar phase, and demixing very often arises during the addition of the cosolvent, which is, itself, aprotic and less polar;
- in the presence of water, DMSO often shows a loss of efficacy, DMSO-water combinations leading to molecular aggregates with a low rate of diffusion;
- the presence of water often results in thickening problems, in particular with cellulose-based thickeners.

Certain monoalcohols also have a good capacity for reducing the crystallization point of DMSO. In general, these alcohols of petrochemical origin are hazard-labelled as being irritant, harmful or toxic and introduce flammability, which is detrimental with respect to DMSO that is free of any hazard labelling.

Formulators are thus currently obliged to use a special installation for heating DMSO drums or to store them and use them in heated premises.

The Applicant Company has sought to solve this problem, and it has found that the addition of diols and/or triols in a content less than the content of a cosolvent in the DMSO, which is usually from 50 to 90 parts by weight of cosolvent in a DMSO+cosolvent mixture, can very efficiently lower the crystallization point of DMSO. Thus, an 80/20 (w/w) DMSO+glycerol mixture has a crystallization point of 0° C.

Furthermore, and unexpectedly, this addition of diol(s) and/or triol(s) allows the production of a mixture that is miscible with the usual, less polar, cosolvents and does not impair the stripping efficacy of DMSO formulated with the diol and/or triol, in contrast with the case where DMSO is formulated with water.

The present invention is thus based on the principle:
- of combining DMSO with an organic compound that contains several hydroxyl groups, promoting the lowering of the crystallization point of DMSO, and which is carbon-based, affording good miscibility with the other conventional organic constituents of stripping and cleaning compositions, such as solvents and activators, and avoiding demixing by moisture uptake (which takes place with water); and
- of producing this combination with a diol and/or triol content that is high enough for efficient lowering of the crystallization point to take place, without, however, reaching the contents of a cosolvent, for which function an alcohol is not recommended since it impairs the stripping efficacy.

Cryobiology (1978), 15(1), 93-108, Boutron P. and Kaufmann A. cites a DMSO+glycerol mixture (10/1 by weight) that is better than pure DMSO for avoiding the crystallization of a eutectic during slow cooling. The said publication does not mention that this mixture is advantageous for lowering the crystallization point of DMSO.

WO 03/048 393 A1 (PCT/IT 01/00611) describes the use of DMSO+glycerol mixtures in an entirely different application, namely the preparation of buffer solutions for the polymerase chain amplification of DNA.

JP 1986-308848 describes, for the microelectronics industry, as a photoresist stripper, a DMSO+propylene glycol mixture used at 100° C. Photoresist stripper formulations are often mixtures based on a dipolar aprotic solvent such as N-methylpyrrolidone or DMSO and a glycol ether. The latter solvent does not serve to lower the crystallization point of the active solvent when it is DMSO. In particular, U.S. Pat. No. 4,401,748, U.S. Pat. No. 4,401,747 and U.S. Pat. No. 4,395,479 mention mixtures based on NMP and diethylene glycol methyl ether. Patent JP 01042653 mentions mixtures based on DMSO and a diethylene glycol monoalkyl ether.

U.S. Pat. No. 5,798,323 and US 2001/0034313 A1 describe photoresist cleaning and stripping compositions based on a solvent and an alkanolamine; among the list of possible solvents are DMSO, ethylene glycol and propylene glycol. DMSO+diol mixtures are not illustrated.

DETAILED DESCRIPTION OF THE INVENTION

A first subject of the present invention is thus the use of at least one diol and/or at least one triol as a dimethyl sulfoxide (DMSO) additive for lowering the crystallization point thereof.

The diol(s) may be chosen from ethylene glycol, propylene glycol and hexylene glycol, and the triol(s) may be chosen from glycerol and 2-ethyl-2-hydroxymethyl-1,3-propanediol.

Mention may be made more particularly of glycerol as a DMSO additive. Glycerol is a "green" additive, which does not lead to any hazard labelling for the DMSO+glycerol combination, DMSO already being free of hazard labelling.

Water may be added to the diol(s) and/or triol(s), in which case sodium chloride may also be added.

The glycerol+water (90/10 w/w) mixture introduced at 20 parts by weight into DMSO (80/18/2 by weight DMSO+glycerol+water mixture) allows lowering of the crystallization point to −2° C. In this case, the water content is only 2% by weight, which does not in any way impair the miscibility properties or the stripping or cleaning efficacy in the case of stripping or cleaning compositions. To achieve this crystallization point using pure water, a water content of 8.5% by weight is needed, which may give rise to demixing problems in certain cases and to inhibition of the stripping or cleaning efficacy.

In the case of the present invention, the amount of water introduced will thus be less than that which gives rise to demixing phenomena in the presence of a cosolvent and to inhibition of the efficacy.

It is also possible to use DMSO+glycerol+water and DMSO+glycerol+water+sodium chloride mixtures, using, if so desired, water+glycerol or glycerol+sodium chloride mixtures, respectively, obtained from industrial manufacture (for example industrial glycerol-containing water formed of about 80% by weight of glycerol+10% by weight of water+10% by weight of sodium chloride). The sodium chloride has the property of further retarding the crystallization.

The DMSO additive may thus be formed, per 100 parts by weight, of
(A) 75 to 100 parts by weight of diol(s) and/or triol(s);
(B) 0 to 15 parts by weight of water; and
(C) 0 to 10 parts by weight of sodium chloride, which may be present only if water is present.

Moreover, the additive constituted by the diol(s) and the triol(s) optionally with the water and the chloride, where appropriate, may represent 5 to 40 parts by weight and in particular 10 to 30 parts by weight per 100 parts by weight of supplemented DMSO.

The present invention also relates to a formulation of dimethyl sulfoxide (DMSO) in combination with the additive as defined above.

The invention also relates to the use of the formulation as defined above as a paint-stripping composition, a surface-cleaning composition, a graffiti-cleaning composition, a surface-cleaning composition in the microelectronics field, such as a photoresist stripper, a DMSO-based agrochemical composition, or as a constituent of an abovementioned composition, as a polymer-dissolving solvent, or as a constituent of a composition that is useful in the field of cosmetology or pharmacy.

The invention also relates to a composition for stripping paints or for cleaning surfaces or graffiti, characterized in that it comprises, per 100 parts by weight of (A)+(B):
(A) 10 to 50 parts by weight of the formulation as defined above; and
(B) 90 to 50 parts by weight of at least one cosolvent chosen from aprotic cosolvents of moderate polarity, especially from ethers, such as methyl tert-butyl ether (MTBE) and anisole, ketones such as methyl ethyl ketone, and esters such as butyl acetate and dibasic esters (mixtures of dimethyl adipate, glutarate and succinate),
and, where appropriate, the usual additives, such as activators, thickeners, softeners and surfactants.

The activators may be chosen from amines and alkanolamines and may be used at up to 10 parts by weight per 100 parts by weight of the DMSO formulation according to the invention+cosolvent(s). The thickeners may be chosen from cellulose-based or acrylic thickeners and may be used at up to 5 parts by weight per 100 parts by weight of the DMSO formulation according to the invention+cosolvent(s).

Finally, the invention relates to a process for stripping paints or for cleaning surfaces or graffiti, characterized in that the stripping or cleaning composition as defined above is applied to the painted surface to be stripped or to the surface to be cleaned or freed of its graffiti, using a brush, the applied composition is left on for 30 minutes, and the flakes of paint and soiling or graffiti are then removed using a paint spatula.

The examples that follow illustrate the present invention without, however, limiting its scope. In the examples, the following abbreviations have been used:
DMSO: dimethyl sulfoxide
MEK: methyl ethyl ketone

EXAMPLE 1

Preparation of a Glycerol-Containing Dimethyl Sulfoxide

A chemical composition having the following formulation, per 100 parts by weight, was prepared;
90 parts by weight of DMSO; and
10 parts by weight of glycerol.

The crystallization point of this composition is about 10° C. This value may be compared with the crystallization point of pure DMSO, which is +18° C.

Paint-Stripping Tests:

This formulation was used to soak at room temperature a piece of cotton wool placed on a wooden board (plywood) coated with a glyptal paint. After 30 minutes of contact, the cotton wool was removed and the plywood was observed at this place.

The same stripping test was performed firstly with pure DMSO and secondly with a formulation containing 90 parts by weight of DMSO and 10 parts by weight of water.

Figure 2:
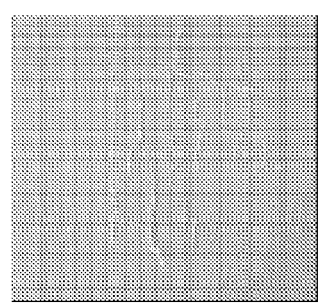
Figure 3:
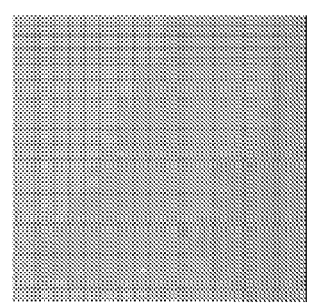

The visual results of these three tests may be seen in FIGS. 1 to 3. It may be seen that, while water has an inhibitory effect on stripping (FIG. 3), this is not the case for glycerol (FIG. 2). Thus, the stripping effect is substantially the same for pure DMSO (FIG. 1) and for the DMSO+glycerol (90/10 w/w) mixture.

EXAMPLE 2

Preparation of a Glycerol-Containing DMSO+MEK Stripping Composition

Glycerol-containing DMSO was formulated with MEK in the following proportions:
glycerol-containing DMSO: 30% by weight; and
MEK: 70% by weight.
A reference formulation was prepared:
DMSO: 30% by weight; and
MEK: 70% by weight.

The same stripping test as in Example 1 was performed with each of these two formulations.

Figure 4:
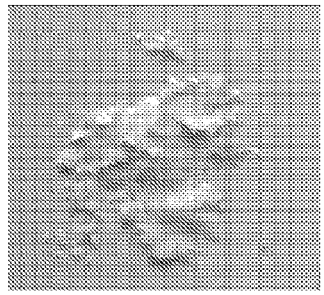
Figure 5:
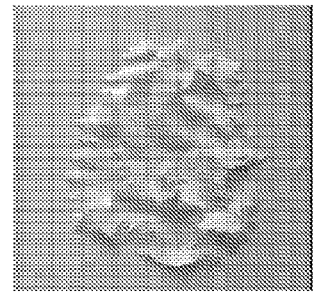

The visual results of these tests may be seen in FIGS. 4 and 5. The effect is the same in both cases, namely the formation of flakes lifted from the support, which is a sign of good stripping efficacy. It is thus confirmed that glycerol has no inhibitory effect on stripping.

The invention claimed is:

1. A method of lowering the crystallization point of dimethyl sulfoxide (DMSO) comprising adding to dimethyl sulfoxide an additive comprising at least one diol and/or triol.

2. Method according to claim 1, characterized in that the diol is selected from the group consisting of ethylene glycol, propylene glycol and hexylene glycol.

3. Method according to claim 1, characterized in that the triol is glycerol.

4. Method according to claim 1, further characterized in adding water to the diol and/or triol.

5. Method according to claim 1, characterized in that the additive comprises, per 100 parts by weight of additive, (A) 75 to 100 parts by weight of diol and/or triol;

(B) 0 to 15 parts by weight of water; and (C) 0 to 10 parts by weight of sodium chloride wherein sodium chloride is present only if water is present.

6. Method according to claim 5, characterized in that the additive comprises 5 to 40 parts by weight per 100 parts by weight of dimethyl sulfoxide and additive.

7. Method according to claim 1, characterized in that the triol is selected from the group consisting of glycerol and 2-ethyl-2-hydroxymethyl-1,3-propanediol.

8. Method of claim 4 further comprising adding sodium chloride with said water.

9. Method of claim 6 wherein additive comprises 10 to 30 parts by weight per 100 parts by weight of dimethyl sulfoxide and additive.

* * * * *